(12) United States Patent
Swazey

(10) Patent No.: US 7,888,308 B2
(45) Date of Patent: Feb. 15, 2011

(54) CATIONIC SURFACTANT SYSTEMS COMPRISING MICROFIBROUS CELLULOSE

(75) Inventor: John M. Swazey, San Diego, CA (US)

(73) Assignee: CP Kelco U.S., Inc., Atlanta, GA (US)

( * ) Notice: Subject to any disclaimer, the term of this patent is extended or adjusted under 35 U.S.C. 154(b) by 0 days.

(21) Appl. No.: 11/612,589

(22) Filed: Dec. 19, 2006

(65) Prior Publication Data
US 2008/0146485 A1 Jun. 19, 2008

(51) Int. Cl.
*C11D 3/22* (2006.01)
*C08B 1/00* (2006.01)

(52) U.S. Cl. .................. 510/470; 510/151; 510/535; 510/473; 510/451; 510/158; 536/56

(58) Field of Classification Search .............. 510/158, 510/451, 504, 535, 470, 151, 473; 424/486, 424/489; 106/162.9; 536/56
See application file for complete search history.

(56) References Cited

U.S. PATENT DOCUMENTS

| | | | |
|---|---|---|---|
| 3,858,854 A | 1/1975 | Win et al. | |
| 4,378,381 A | 3/1983 | Turbak et al. | |
| 4,379,059 A | 4/1983 | Hockey et al. | |
| 4,452,722 A | 6/1984 | Turbak et al. | |
| 4,481,076 A | 11/1984 | Herrick | |
| 4,483,743 A | 11/1984 | Turbak et al. | |
| 4,500,546 A | 2/1985 | Turbak et al. | |
| 5,087,471 A | 2/1992 | Combes et al. | |
| 5,738,897 A * | 4/1998 | Gidley et al. | 426/573 |
| 5,951,910 A * | 9/1999 | Skaggs et al. | 252/70 |
| 6,071,727 A * | 6/2000 | Bungay et al. | 435/101 |
| 6,224,663 B1 | 5/2001 | Cantiani et al. | |
| 6,241,812 B1 | 6/2001 | Smith et al. | |
| 6,258,771 B1 * | 7/2001 | Hsu et al. | 510/418 |
| 6,302,209 B1 | 10/2001 | Thompson et al. | |
| 6,620,775 B2 * | 9/2003 | Winston et al. | 510/470 |
| 6,673,371 B2 * | 1/2004 | Brown et al. | 424/486 |
| 6,846,785 B2 | 1/2005 | Patel | |
| 6,967,027 B1 | 11/2005 | Heux et al. | |
| 2003/0109391 A1 | 6/2003 | Midha et al. | |
| 2003/0162689 A1 * | 8/2003 | Schymitzek et al. | 510/515 |
| 2004/0267006 A1 | 12/2004 | Yamane et al. | |
| 2005/0244365 A1 * | 11/2005 | Labib et al. | 424/78.18 |
| 2006/0083761 A1 | 4/2006 | Yoshimi et al. | |
| 2006/0110416 A1 | 5/2006 | Ryles et al. | |
| 2006/0281859 A1 | 12/2006 | Suzuki et al. | |
| 2007/0027108 A1 | 2/2007 | Yang et al. | |
| 2007/0197779 A1 * | 8/2007 | Yang et al. | 536/2 |
| 2008/0108541 A1 * | 5/2008 | Swazey | 510/535 |
| 2010/0009891 A1 * | 1/2010 | Canto et al. | 510/418 |
| 2010/0016575 A1 * | 1/2010 | Yang et al. | 536/56 |

FOREIGN PATENT DOCUMENTS

| | | |
|---|---|---|
| DE | 10215602 | 10/2003 |
| GB | 2379223 A | 3/2003 |
| WO | WO 9940153 A1 * | 8/1999 |
| WO | 0105838 A1 | 1/2001 |
| WO | 02018486 | 3/2002 |
| WO | WO 02/18486 A2 * | 3/2002 |
| WO | 2004074420 A1 | 9/2004 |

OTHER PUBLICATIONS

Journal Article: Ronald Deis. Reducing Fat: A Cutting-Edge Strategy. Food Product Design, Mar. 1997. (see Microbial Web section, para. 6-15).*
Article: Garcia et al. Food Applications of the New Polysaccharides Technology. The IPTS Report, Issue 20, Dec. 1997. (see Bacterial Cellulose or Microfibrous Cellulose section, para. 13-17).*
PCT Search Report for PCT/US07/87216, Date of mailing May 6, 2008.
PCT Search Report for PCT/US07/87216, mailed May 6, 2008.
PCT Search Report for PCT/US07/83422, mailed Mar. 19, 2008.
PCT Search Report for PCT/US07/87229, mailed Apr. 9, 2008.
Extended European Search Report for EP07865568.5, mailed Aug. 8, 2010.
Disclosure Under 37 C.F.R. 1.56.

* cited by examiner

*Primary Examiner*—Mark Eashoo
*Assistant Examiner*—Jane L Stanley
(74) *Attorney, Agent, or Firm*—Sutherland Asbill & Brennan LLP

(57) ABSTRACT

Cationic surfactant systems, using microfibrous cellulose to suspend particulates therein, are described. Methods of making these systems are also described.

20 Claims, No Drawings

CATIONIC SURFACTANT SYSTEMS COMPRISING MICROFIBROUS CELLULOSE

BACKGROUND OF THE INVENTION

Cationic surfactant-based products such as anti-bacterial surface cleaners, fabric softeners, skin conditioners, hair conditioners, conditioning shampoos, among others, are often difficult to thicken with conventional thickeners. Many common thickeners such as xanthan gum, CMC (carboxymethylcellulose), carrageenan, and polyacrylates are anionic and therefore, can react with the cationic surfactants and cause precipitation of the cationic and thickener or reduce the efficacy of the cationic surfactant. Non-ionic thickeners such as hydroxyethylcellulose (HEC), hydroxypropylmethylcellulose (HPMC), and scleroglucan can provide viscosity in cationic systems, however in the case of HEC and HPMC, very little suspension properties are imparted to the fluid. In the case of scleroglucan, good suspension is often achieved but cost-in use can be prohibitive. Cationic thickeners such as polyquaternium 10 (cationic HEC) and cationic guar provide thickening in cationic systems but not suspension. Some forms of polyacrylates are effective at thickening cationic systems but they can be limited by pH, require high concentrations, have high cost-in-use, and often have narrow limits of compatibility with the cationic surfactants.

There is a need in industry to provide reliable suspension and viscosity to cationic surfactant systems. In these systems, the suspension of particles is often desired and such particulates might include abrasive agents, aesthetic agents (decorative beads, pearlescents, air bubbles, fragrance beads, etc.) or active ingredients (insoluble enzymes, encapsulated actives such as moisturizers, zeolites, exfoliating agents (e.g. alpha hydroxyl and/or glycolic acids or polyethylene beads), vitamins (e.g. vitamin E)) etc. or both.

It has been discovered that microfibrous cellulose (MFC), bacterially derived or otherwise, can be used to provide suspension of particulates in cationic systems. It was also discovered that the MFC may be used for this purpose with or without co-agents. When bacterially-derived microfibrous cellulose is utilized, cellular debris can be eliminated which can also result in transparent solutions at typical use levels with some formulations.

The microfibrous cellulose is non-ionic and is therefore unaffected by the cationic surfactants and maintains good suspension in these systems. Microfibrous cellulose is unique in its ability to function in these systems in part because it is dispersed rather than solubilized, thereby allowing its use in a wide range of pH and cationic surfactant concentrations without concern of precipitating the polymer due to "salting out" or other effects related to the competition for water.

BRIEF SUMMARY OF THE INVENTION

Cationic surfactant systems comprising microfibrous cellulose are described. "Cationic systems" is intended to include but is not limited to cationic surfactants used in industrial and personal care applications for anti-microbial, fabric softening, and skin and hair conditioning. Microfibrous cellulose (MFC) includes MFC prepared by microbial fermentation or MFC prepared by mechanically disrupting/altering cereal, wood, or cotton-based cellulose fibers. When bacterially-derived microfibrous cellulose is utilized, cellular debris can be eliminated which results in transparent solutions at typical use levels. The present invention utilizes MFC to provide suspension of particulates in formulations containing cationic surfactants.

The cationic surfactant concentration of these systems ranges from about 0.1% to about 50% (w/w active surfactant) wherein the specific concentration is product dependent. Anti-bacterial household surface cleaners typically contain about 0.1% to about 4% (w/w) active cationic surfactant, hair and skin conditioners typically contain about 0.5% to about 3% cationic surfactants, and fabric softeners typically contain about 3% to about 15% (w/w) cationic surfactant (with 15% being a "concentrated" fabric softener product). Concentrates of the cationic surfactants can also be thickened for later dilution into formulated products. These concentrates can contain greater than 50% active cationic surfactant.

The MFC is present at concentrations from about 0.05% to about 1.0%, but the concentration will depend on the desired product. For example, while about 0.06% (w/w) MFC is preferred for suspending small alginate beads in a household cleaner containing 4% of the anti-bacterial cationic surfactant, benzylalkonium chloride, about 0.075% is preferred for suspending air bubbles in fabric softener.

Particulates to be suspended could include abrasive agents, aesthetic agents (decorative beads, pearlescents, air bubbles, fragrance beads, etc.) or active ingredients (insoluble enzymes, encapsulated actives such as moisturizers, zeolites, exfoliating agents (e.g. alpha hydroxyl and/or glycolic acids or polyethylene beads), vitamins (e.g. vitamin E) etc. or both. Other suitable particulates would be apparent to one of skill in the art.

The invention is also directed to the use of co-agents and/or co-processing agents such as cationic HEC, cationic guar and/or guar gum with the microfibrous cellulose in the surfactant systems described herein. Microfibrous cellulose blends are microfibrous cellulose products which contain co-agents. Four blends are described MFC, cationic guar, and guar in a ratio of 6:3:1, MFC and cationic guar in a ratio of 1:1 and 3:2 and MFC and cationic HEC in a ratio of 1:1. These blends allow MFC to be prepared as a dry product which can be "activated" with high shear or high extensional mixing into water or other water-based solutions. "Activation" occurs when the MFC blends are added to water and the co-agents/co-processing agents are hydrated. After the hydration of the co-agents/co-processing agents, high shear is generally then needed to effectively disperse the microfibrous cellulose fibers to produce a three-dimensional functional network that exhibits a true yield point.

The invention is further directed to methods of making the cationic surfactant systems described, with or without co-agents and/or co-processing agents.

BRIEF DESCRIPTION OF THE SEVERAL VIEWS OF THE DRAWINGS

The foregoing summary will be better understood when read in conjunction with the Detailed Description of the Invention.

DETAILED DESCRIPTION OF THE INVENTION

A simplified anti-bacterial hard surface cleaner formulation demonstrating the cationic surfactant compatibility with 4% benzylalkonium chloride and suspension properties using a 0.15% MFC/cationic guar (1:1) blend are described in Example 1. The cleaner exhibits the ability to suspend beads.

Example 2 describes a concentrated commercial liquid fabric softener with about 7.5% cationic surfactant and 0.15% MFC/cationic guar (1:1) blend and alginate suspended therein.

A conditioning hair spray containing cationic surfactant and a 0.125% MFC/cationic guar (6:4) blend. This product has suspended glitter and is described in Example 3.

A wet-cake form of microfibrous cellulose was used in Example 4 for preparing a high cationic surfactant system comprising a concentrated benzylalkonium solution. The 40% benzylalkonium chloride and 0.06% active MFC solution exhibits the ability to suspend alginate beads and is described in Example 4.

A wet-cake form of microfibrous cellulose was used in Example 4 for preparing a high cationic surfactant system comprising a concentrated benzylalkonium solution. The 50% benzylalkonium chloride and 0.075% active MFC solution exhibits the ability to suspend air bubbles and is described in Example 5.

EXAMPLE 1

A simplified anti-bacterial hard surface cleaner containing 4% benzylalkonium chloride with suspended alginate beads was prepared. The cleaner exhibited a measurable yield value and possessed the ability to suspend air bubbles and beads. A yield value of 0.82 Pa (as measured with a Brookfield® Yield Rheometer) was obtained. A concentrate was first prepared containing 0.3% microfibrous cellulose blend (MFC/cationic guar 1:1 blend) in deionized water. The concentrate was made by mixing the solution on an Oster® blender at "liquefy" (top speed) for 5 minutes. The microfibrous cellulose mixture was then diluted 1:1 with an 8% solution of benzylalkonium chloride. The cationic solution was added to the microfibrous cellulose solution while mixing at about 600 rpm with a jiffy mixing blade. Alginate beads were added to demonstrate suspension. Excellent suspension of air and/or alginate beads was achieved with no settling observed at room temperature or at 45° C. for 3 months. The microfibrous cellulose diluted well notwithstanding the relative low shear of the jiffy or propeller mixing blade.

EXAMPLE 2

A concentrated commercial fabric softener containing about 7.5% cationic surfactant was prepared. "Downy® Clean Breeze™ ultra concentrated" liquid fabric softener was modified with MFC. A 0.3% microfibrous cellulose blend (MFC/cationic guar 1:1 blend) concentrate was activated in distilled water with an Oster® blender set at top speed (liquefy) by mixing for 5 minutes. The microfibrous cellulose solution was diluted 1:1 with Downy® ultra concentrated fabric softener while mixing at about 600 rpm with a jiffy mixing blade. Alginate beads were added to test suspension. Very good suspension of the beads was achieved for the dilution resulting in a yield point of 1.4 Pa (as measured with a Brookfield® Yield Rheometer). The fabric softener was put in a 45° C. oven to assess heat stability and showed excellent stability with no loss in suspension over 4 weeks of aging.

EXAMPLE 3

A conditioning hair spray with glitter suspended therein was prepared. The resulting hair spray exhibited good spray characteristics and excellent suspension properties. A yield value of about 0.2 Pa (as measured with a Brookfield® Yield Rheometer) was obtained.

Step A: Deionizied water and disodium EDTA were added to a small Oster® mixing jar. Microfibrous cellulose (MFC/cationic guar 6:4 blend) was added to the top of the water and then the Oster® mixer blade was assembled and the combination was mixed at top speed for 5 minutes ("Liquify" speed).

Step B: STS and fragrance were mixed with pre-warmed RH-40 and propylene glycol and solubilized in the water phase.

Step C: The remaining ingredients were added sequentially and mixed. The result was a low viscosity, sprayable hair conditioner with glitter suspended therein and a pH of 4.8.

TABLE 1

Sprayable Hair Conditioner with Suspension Properties

| Process Step | Ingredient | % (w/w) | Grams |
|---|---|---|---|
| A | Deionized Water | 93.725 | 374.9 |
| A | Microfibrous Cellulose blend (MFC/cationic guar 6:4 blend) | 0.125 | 0.5 |
| A | Disodium EDTA | 0.1 | 0.4 |
| B | Fragrance | To Suit | |
| B | Crodamol STS | 0.5 | 2 |
| B | Cremophor RH 40 | 1.5 | 6 |
| B | Propylene glycol | 0.75 | 3 |
| C | CTAC 29 (29% Cetrimonium Chloride, a cationic conditioning agent) | 1 | 4 |
| C | Wheat Protein | 1 | 4 |
| C | Panthenol | 0.2 | 0.8 |
| C | Acetamide MEA | 1 | 4 |
| C | Kathon | 0.1 | 0.4 |
| C | Color | To Suit | To Suit |
| C | Glitter | To Suit | To Suit |
| Totals | | 100.00 | 400.00 |

EXAMPLE 4

High cationic surfactant systems were prepared having a 40% concentration of benzylalkonium chloride and the wet-cake version of microfibrous cellulose. Alginate beads or air was suspended in the solutions. A concentrate of 1.85% wet-cake microfibrous cellulose was activated in distilled water with an Oster® blender set at top speed (liquefy) by mixing for 5 minutes. The microfibrous cellulose solution was diluted by 80% with a 50% benzylalkonium chloride solution while mixing at 600 rpm with a jiffy mixing blade. Alginate beads were added to test suspension. The activity (% solids) of this wet-cake form of MFC was about 16% yielding an active MFC level of 0.06% in the final solution. Upon visual inspection, good suspension was achieved for the dilution resulting in a yield point of 0.36 Pa (as measured with a Brookfield® Yield Rheometer).

EXAMPLE 5

High cationic surfactant systems were prepared having about 50% concentration of benzylalkonium chloride and the wet-cake version of microfibrous cellulose. Air was suspended in the solution. 0.47% wet-cake microfibrous cellulose was activated in a 50% concentrate of benzylalkonium chloride solution with an Oster® blender set at top speed (liquefy) by mixing for 5 minutes. The activity (% solids) of this wet-cake form of MFC was 16% yielding an active MFC level of 0.075% in the final solution. Upon visual inspection, good suspension of air was achieved for the dilution resulting in a yield point of 4.5 Pa. Clarity was very good with only a slight haze.

The invention claimed is:

1. An aqueous composition comprising a cationic surfactant system consisting essentially of (i) microfibrous cellulose at a concentration of about 0.06% to about 0.075% (w/w), (ii) at least one cationic surfactant at a concentration between about 40% and about 50% (w/w active surfactant), and (iii) a suspended particulate.

2. The composition according to claim 1, wherein the microfibrous cellulose concentration is about 0.075%.

3. The composition according to claim 1, wherein the particulate is selected from the group consisting of air bubbles, beads, and any combination thereof.

4. The composition of claim 1, wherein the microfibrous cellulose is bacterially derived.

5. The composition of claim 1, wherein the cationic surfactant system is transparent.

6. The composition of claim 1, wherein the microfibrous cellulose is dispersed and not appreciably solubilized.

7. The composition of claim 1, wherein the aqueous composition has a Yield Point selected from 1.4, 0.2, 0.36, and 4.5 Pa.

8. The composition of claim 1, wherein the cationic surfactant system does not contain a co-agent.

9. Method of preparing an aqueous composition comprising a cationic surfactant system consisting essentially of:
    combining microfibrous cellulose with water and mixing,
    adding cationic surfactant and then mixing, and
    adding a particulate followed by mixing,
    wherein the resulting cationic surfactant system is clear and the particulates are suspended therein and wherein the microfibrous cellulose is present at a concentration between about 0.05% and about 0.09% (w/w) and the cationic surfactant is present at a concentration between about 40% and about 50% (w/w active surfactant).

10. The method of claim 9, wherein the microfibrous cellulose concentration is between about 0.06% and about 0.075%.

11. The method of claim 9, wherein the microfibrous cellulose concentration is about 0.075%.

12. The method of claim 9, wherein the microfibrous cellulose concentration is between about 0.05% and about 0.075%.

13. The method of claim 9, wherein the microfibrous cellulose is bacterially derived.

14. The method of claim 9, wherein the method results in a stable cationic surfactant system wherein the microfibrous cellulose is dispersed and not appreciably solubilized.

15. The method of claim 9, resulting in an aqueous composition having a Yield Point selected from 1.4, 0.2, 0.36, and 4.5 Pa.

16. The method of claim 9, wherein the cationic surfactant system does not contain a co-agent.

17. An aqueous composition comprising a cationic surfactant system consisting essentially of (i) microfibrous cellulose at a concentration between about 0.05% and about 1.0% (w/w), (ii) at least one cationic surfactant at a concentration between about 40% and about 50% (w/w active surfactant), and (iii) a suspended particulate.

18. The composition of claim 17, wherein the microfibrous cellulose concentration is between about 0.05% and about 0.09%.

19. A method of preparing an aqueous composition comprising a cationic surfactant system consisting essentially of:
    combining a microfibrous cellulose with water and mixing,
    adding cationic surfactant and then mixing, and
    adding a particulate followed by mixing,
    wherein the resulting cationic surfactant system is clear and the particulates are suspended therein and wherein the microfibrous cellulose is present at a concentration between about 0.05% and about 1% and the cationic surfactant is present at a concentration between about 40% and about 50% (w/w active surfactant).

20. The method of claim 19, wherein the microfibrous cellulose concentration is between about 0.05% and about 0.09%.

* * * * *